(12) United States Patent
Klaassen et al.

(10) Patent No.: US 9,701,972 B2
(45) Date of Patent: Jul. 11, 2017

(54) PENTOSE SUGAR FERMENTING CELL (75) Inventors: Paul Klaassen, Echt (NL); Gijsberdina Pieternella Van Suylekom, Echt (NL); Rene Marcel De Jong, Echt (NL)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 14/236,191

(22) PCT Filed: Aug. 2, 2012

(86) PCT No.: PCT/EP2012/065088
§ 371 (c)(1),
(2), (4) Date: Jan. 30, 2014

(87) PCT Pub. No.: WO2013/017644
PCT Pub. Date: Feb. 7, 2013

(65) Prior Publication Data
US 2014/0162312 A1  Jun. 12, 2014

Related U.S. Application Data
(60) Provisional application No. 61/515,014, filed on Aug. 4, 2011.

(30) Foreign Application Priority Data
Aug. 4, 2011 (EP) .................... 11176601

(51) Int. Cl.
| | | |
|---|---|---|
| C12N 15/81 | (2006.01) |
| C12N 9/92 | (2006.01) |
| C12P 7/10 | (2006.01) |
| C12P 7/16 | (2006.01) |
| C12P 7/18 | (2006.01) |
| C12P 7/20 | (2006.01) |
| C12P 7/40 | (2006.01) |
| C12P 7/42 | (2006.01) |
| C12P 7/46 | (2006.01) |
| C12P 7/48 | (2006.01) |
| C12P 7/54 | (2006.01) |
| C12P 7/56 | (2006.01) |
| C12P 5/02 | (2006.01) |
| C12P 7/06 | (2006.01) |
| C12P 35/00 | (2006.01) |

(52) U.S. Cl.
CPC ............... *C12N 15/81* (2013.01); *C12N 9/92* (2013.01); *C12N 15/815* (2013.01); *C12P 5/026* (2013.01); *C12P 7/06* (2013.01); *C12P 7/10* (2013.01); *C12P 7/16* (2013.01); *C12P 7/18* (2013.01); *C12P 7/20* (2013.01); *C12P 7/40* (2013.01); *C12P 7/42* (2013.01); *C12P 7/46* (2013.01); *C12P 7/48* (2013.01); *C12P 7/54* (2013.01); *C12P 7/56* (2013.01); *C12P 35/00* (2013.01); *C12Y 503/01005* (2013.01); *Y02E 50/16* (2013.01); *Y02E 50/17* (2013.01)

(58) Field of Classification Search
None
See application file for complete search history.

(56) References Cited

U.S. PATENT DOCUMENTS

| | | |
|---|---|---|
| 8,399,215 B2 | 3/2013 | Klaassen et al. |
| 2012/0034648 A1 | 2/2012 | Klaassen et al. |

FOREIGN PATENT DOCUMENTS

| | | | |
|---|---|---|---|
| WO | 2009109633 A1 | 9/2009 | |
| WO | 2010074577 A1 | 7/2010 | |
| WO | WO2010074577 | * 7/2010 | ............... C12N 1/14 |

OTHER PUBLICATIONS

Cbei_2383 xylose isomerase[Clostridium beijerinckii NCIMB 8052] Text. Gene ID: 5293587, discontinued on Feb. 6, 2015.
Copeland, "RecName: Full=Xylose isomerase; EC=5.3.1.5", from EBI accession No. UNIPROT:A6LW13, Jul. 24, 2007, XP002664799.
Yang, Gu, et al. "Reconstruction of xylose utilization pathway and regulons in Firmicutes", BioMed Central Ltd., BMC Genomics 2010, 11:255.
International Search Report corresponding to PCT/EP2012/065088 mailed Oct. 31, 2012.
Brat, Dawid et al., "Functional Expression of a Bacterial Xylose Isomerase in *Saccharomyces cerevisiae*", Applied and Environmental Microbiology, Apr. 2009, pp. 2304-2311, vol. 75, No. 8.

* cited by examiner

*Primary Examiner* — Paul Holland
(74) *Attorney, Agent, or Firm* — McBee Moore Woodward & Vanik IP, LLC (57) ABSTRACT

The invention relates to a cell which comprises a nucleotide sequence encoding a xylose isomerase, wherein the amino acid sequence of the xylose isomerase has at least 75% sequence identity to the amino acid sequence set out in SEQ ID NO: 2 and wherein the nucleotide sequence is heterologous to the host. A cell of the invention may be used in a process for producing a fermentation product, such as ethanol. Such a process may comprise fermenting a medium containing a source of xylose with a cell of the invention such that the cell ferments xylose to the fermentation product.

13 Claims, 3 Drawing Sheets

PENTOSE SUGAR FERMENTING CELL

CROSS REFERENCE TO RELATED APPLICATIONS

This application is a §371 National Stage Application of PCT/EP2012/065088, filed Aug. 2, 2012, which claims priority to European Application No. 11176601.0, filed Aug. 4, 2011, and to U.S. Provisional Application No. 61/515,014, filed Aug. 4, 2011.

BACKGROUND OF THE INVENTION

Field of the Invention

The present invention relates to a cell which is capable of isomerising xylose to xylulose. The invention also relates to a process in which such cells are used for the production of a fermentation product, such as ethanol.

Description of Related Art

Large-scale consumption of traditional, fossil fuels (petroleum-based fuels) in recent decades has contributed to high levels of pollution. This, along with the realisation that the world stock of fossil fuels is not limited and a growing environmental awareness, has stimulated new initiatives to investigate the feasibility of alternative fuels such as ethanol, which is a particulate-free burning fuel source that releases less $CO_2$ than unleaded gasoline on a per liter basis.

Although biomass-derived ethanol may be produced by the fermentation of hexose sugars obtained from many different sources, the substrates typically used for commercial scale production of fuel alcohol, such as cane sugar and corn starch, are expensive. Increases in the production of fuel ethanol will therefore require the use of lower-cost feedstocks.

Currently, only lignocellulosic feedstock derived from plant biomass is available in sufficient quantities to substitute the crops currently used for ethanol production. In most lignocellulosic material, the second-most-common sugar, after glucose, is xylose. Thus, for an economically feasible fuel production process, both hexose and pentose sugars must be fermented to form ethanol. The yeast *Saccharomyces cerevisiae* is robust and well adapted for ethanol production, but it is unable to produce ethanol using xylose as a carbon source. Also, no naturally-occurring organisms are known which can ferment xylose to ethanol with both a high ethanol yield and a high ethanol productivity. There is therefore a need for an organism possessing these properties so as to enable the commercially-viable production of ethanol from lignocellulosic feedstocks.

SUMMARY

According to the invention, there is provided a cell that is capable of fermentation, such as alcoholic fermentation, and of using xylose as a carbon source. Such a cell comprises a nucleotide sequence encoding a xylose isomerase, wherein the amino acid sequence of the xylose isomerase has at least 75% sequence identity to the amino acid sequence set out in SEQ ID NO: 2 and wherein the nucleotide sequence is heterologous to the host. Such a cell produces a higher amount of ethanol when using xylose as a carbon source as compared to the wild type filamentous fungus.

The invention also provides:

a process for producing a fermentation product which process comprises fermenting a medium containing a source of xylose with a cell of the invention such that the cell ferments xylose to the fermentation product;

a process for producing a fermentation product which process comprises fermenting a medium containing at least a source of xylose and a source of L-arabinose with a cell as defined of the invention which is also capable of utilizing L-arabinose such that the cell ferments xylose and L-arabinose to the fermentation product; and a process for producing a fermentation product which process comprises fermenting a medium containing at least a source of xylose and a source of L-arabinose with a cell of the invention and a cell able to use L-arabinose, whereby each cell ferments xylose and/or arabinose to the fermentation product.

In an embodiment, the cell comprises a nucleotide sequence encoding a xylose isomerase obtainable from a cell of genus *Clostridium*, e.g. from a *Clostridium beijerinckii* cell. In an embodiment, the nucleotide may be wild-type or codon optimized or codon pair optimized.

The invention further provides the use of a cell of the invention in a process for the production of a fermentation product.

BRIEF DESCRIPTION OF THE SEQUENCE LISTING

SEQ ID NO: 1 sets out the codon pair optimised xylose isomerase sequence from *Clostridium beijerinckii*.
SEQ ID NO: 2 sets out the amino acid sequence of xylose isomerase from *Clostridium beijerinckii*.
SEQ ID NO: 3 sets out the sequence of forward primer.
SEQ ID NO: 4 sets out the sequence of reverse primer.

DETAILED DESCRIPTION OF A PREFERRED EMBODIMENT

Throughout the present specification and the accompanying claims the words "comprise" and "include" and variations such as "comprises", "comprising", "includes" and "including" are to be interpreted inclusively. That is, these words are intended to convey the possible inclusion of other elements or integers not specifically recited, where the context allows.

The invention relates to a cell which comprises a nucleotide sequence encoding a xylose isomerase, wherein the amino acid sequence of the xylose isomerase has at least 75% identity to the amino acid sequence set out in SEQ ID NO: 2 and wherein the nucleotide sequence is heterologous to the host.

The presence of the nucleotide sequence encoding a xylose isomerase confers on the cell the ability to isomerise xylose to xylulose.

A "xylose isomerase" (EC 5.3.1.5) is herein defined as an enzyme that catalyses the direct isomerisation of D-xylose into D-xylulose and/or vice versa. The enzyme is also known as a D-xylose ketoisomerase. A xylose isomerase herein may also be capable of catalysing the conversion between D-glucose and D-fructose (and accordingly may therefore be referred to as a glucose isomerase). A xylose isomerase herein may require a bivalent cation, such as magnesium, manganese or cobalt as a cofactor.

Accordingly, a cell of the invention is capable of isomerising xylose to xylulose. The ability of isomerising xylose to xylulose is conferred on the host cell by transformation of the host cell with a nucleic acid construct comprising a nucleotide sequence encoding a defined xylose isomerase. A cell of the invention isomerises xylose into xylulose by the direct isomerisation of xylose to xylulose. This is understood to mean that xylose is isomerised into xylulose in a single reaction catalysed by a xylose isomerase, as opposed to two step conversion of xylose into xylulose via a xylitol intermediate as catalysed by xylose reductase and xylitol dehydrogenase, respectively.

A unit (U) of xylose isomerase activity may herein be defined as the amount of enzyme producing 1 nmol of xylulose per minute, under conditions as described by Kuyper et al. (2003, FEMS Yeast Res. 4: 69-78).

The cell of the invention is defined with reference to a xylose isomerase having the amino acid sequence of SEQ ID NO: 2 or a sequence having at least 74% sequence identity thereto. Likewise, a cell of the invention may be defined with reference to a xylose isomerase be a nucleotide sequence which encoding such an amino acid sequence.

SEQ ID NO: 2 sets out the amino acid sequence of xylose isomerase from *Clostridium beijerinckii*. A cell of the invention comprises a nucleotide sequence encoding a xylose isomerase having the amino acid of SEQ ID NO: 2 or one which has at least 74% sequence identity thereto.

Preferably, a cell according to the present invention is a cell comprising a nucleotide sequence encoding a xylose isomerase having a sequence which has at least about 75%, preferably at least about 80%, at least about 85%, at least about 90%, at least about 92%, at least about 93%, at least about 94%, at least about 95%, at least about 96%, at least about 97%, at least about 98% or at least about 99% or at least 75%, at least 80%, at least 85%, at least 90%, at least 92%, at least 93%, at least 94%, at least 95%, at least 96%, at least 97%, at least 98% or at least 99% sequence identity with the amino acid sequence of SEQ ID NO:2. A cell according to the present invention may comprise a nucleotide sequence encoding a xylose isomerase having a sequence which has at least about 50%, at least about 55%, at least about 60%, at least about 70%, at least about 75%, preferably at least about 80%, at least about 85%, at least about 90%, at least about 92%, at least about 93%, at least about 94%, at least about 95%, at least about 96%, at least about 97%, at least about 98% or at least about 99% or at least 75%, at least 80%, at least 85%, at least 90%, at least 92%, at least 93%, at least 94%, at least 95%, at least 96%, at least 97%, at least 98% or at least 99% sequence identity with the nucleic acid sequence set out in SEQ ID NO: 1.

Sequence identity (or sequence similarity) is herein defined as a relationship between two or more amino acid (polypeptide or protein) sequences or two or more nucleic acid (polynucleotide) sequences, as determined by comparing the sequences. Usually, sequence identities or similarities are compared, typically over the whole length of the sequences compared. However, sequences may be compared over shorter comparison windows. In the art, "identity" also means the degree of sequence relatedness between amino acid or nucleic acid sequences, as the case may be, as determined by the match between strings of such sequences.

Preferred methods to determine identity are designed to give the largest match between the sequences tested. Methods to determine identity and similarity are codified in publicly available computer programs. Preferred computer program methods to determine identity and similarity between two sequences include e.g. the BestFit, BLASTP, BLASTN, and FASTA (Altschul, S. F. et al., J. Mol. Biol. 215:403-410 (1990), publicly available from NCBI and other sources (BLAST Manual, Altschul, S., et al., NCBI NLM NIH Bethesda, Md. 20894). Preferred parameters for amino acid sequences comparison using BLASTP are gap open 11.0, gap extend 1, Blosum 62 matrix. Preferred parameters for nucleic acid sequences comparison using BLASTP are gap open 11.0, gap extend 1, DNA full matrix (DNA identity matrix).

Optionally, in determining the degree of amino acid similarity, the skilled person may also take into account so-called "conservative" amino acid substitutions, as will be clear to the skilled person.

Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulphur-containing side chains is cysteine and methionine.

Preferred conservative amino acids substitution groups are: valine-leucine-isoleucine, phenylalanine-tyrosine, lysine-arginine, alanine-valine, and asparagine-glutamine. Substitutional variants of the amino acid sequence disclosed herein are those in which at least one residue in the disclosed sequences has been removed and a different residue inserted in its place. Preferably, the amino acid change is conservative. Preferred conservative substitutions for each of the naturally occurring amino acids are as follows: Ala to ser; Arg to lys; Asn to gln or his; Asp to glu; Cys to ser or ala; Gln to asn; Glu to asp; Gly to pro; His to asn or gln; He to leu or val; Leu to ile or val; Lys to arg; gln or glu; Met to leu or ile; Phe to met, leu or tyr; Ser to thr; Thr to ser; Trp to tyr; Tyr to trp or phe; and, Val to ile or leu.

A nucleotide sequence encoding an enzyme which catalyses the conversion of xylose to xylulose according to the invention may also be defined by its capability to hybridise with the nucleotide sequences encoding the enzyme having the sequence set out in SEQ ID NO: 2 or a sequence having at least 74% sequence identity therewith, under moderate, or preferably under stringent hybridisation conditions.

Formally, such nucleotide sequences hybridize with the reverse complement of the nucleotide sequences which encode the enzyme having the sequence set out in SEQ ID NO: 2 or a sequence having at least 74% sequence identity therewith, for examples sequences which hybridize with the reverse complement of SEQ ID NOs: 1 or 2.

Stringent hybridisation conditions are herein defined as conditions that allow a nucleic acid sequence of at least about 25, preferably about 50 nucleotides, 75 or 100 and most preferably of about 200 or more nucleotides, to hybridise at a temperature of about 65° C. in a solution comprising about 1 M salt, preferably 6×SSC (sodium chloride, sodium citrate) or any other solution having a comparable ionic strength, and washing at 65° C. in a solution comprising about 0.1 M salt, or less, preferably 0.2×SSC or any other solution having a comparable ionic strength. Preferably, the hybridisation is performed overnight, i.e. at least for 10 hours and preferably washing is performed for at least one hour with at least two changes of the washing solution. These conditions will usually allow the specific hybridisation of sequences having about 90% or more sequence identity.

Moderate conditions are herein defined as conditions that allow a nucleic acid sequences of at least 50 nucleotides, preferably of about 200 or more nucleotides, to hybridise at a temperature of about 45° C. in a solution comprising about 1 M salt, preferably 6×SSC or any other solution having a comparable ionic strength, and washing at room temperature in a solution comprising about 1 M salt, preferably 6×SSC or any other solution having a comparable ionic strength. Preferably, the hybridisation is performed overnight, i.e. at least for 10 hours, and preferably washing is performed for at least one hour with at least two changes of the washing solution. These conditions will usually allow the specific hybridisation of sequences having up to 50% sequence identity. The person skilled in the art will be able to modify these hybridisation conditions in order to specifically identify sequences varying in identity between 50% and 90%.

To increase the likelihood that the introduced enzyme is expressed in active form in a cell of the invention, the corresponding encoding nucleotide sequence may be adapted to optimise its codon usage to that of the chosen yeast cell. Several methods for codon optimisation are known in the art. A preferred method to optimise codon usage of the nucleotide sequences to that of the yeast is a codon pair optimization technology as disclosed in WO2006/077258 and/or WO2008/000632. WO2008/000632 addresses codon-pair optimization. Codon-pair optimisation is a method wherein the nucleotide sequences encoding a polypeptide are modified with respect to their codon-usage, in particular the codon-pairs that are used, to obtain improved expression of the nucleotide sequence encoding the polypeptide and/or improved production of the encoded polypeptide. Codon pairs are defined as a set of two subsequent triplets (codons) in a coding sequence.

As a simple measure for gene expression and translation efficiency, herein, the Codon Adaptation Index (CAI), as described in Xuhua Xia, Evolutionary Bioinformatics 2007; 3 53-58, is used. The index uses a reference set of highly expressed genes from a species to assess the relative merits of each codon, and a score for a gene is calculated from the frequency of use of all codons in that gene. The index assesses the extent to which selection has been effective in moulding the pattern of codon usage. In that respect it is useful for predicting the level of expression of a gene, for assessing the adaptation of viral genes to their hosts, and for making comparisons of codon usage in different organisms. The index may also give an approximate indication of the likely success of heterologous gene expression. In the codon pair optimized genes according to the invention, the CAI is 0.6 or more, 0.7 or more, 0.8 or more, 0.85 or more, 0.87 or more 0.90 or more, 0.95 or more, or about 1.0.

In a cell of the invention, the xylose isomerase is typically heterologous to the cell. That is to say, the xylose isomerase has a sequence which does not naturally occur in the cell in question as part of the organism, cell, genome DNA or RNA sequence in which it is present. That is to say, the xylose isomerase is exogenous to the cell or does not occur naturally in the cell. Accordingly, a nucleotide sequence encoding a xylose isomerase is typically expressed or is capable of being expressed in active form in the transformed host cell.

A cell of the invention is thus a cell that comprises, i.e. has been transformed with, a nucleic acid construct comprising the nucleotide sequence encoding the xylose isomerase as defined above. The nucleic acid construct comprising the xylose isomerase coding sequence preferably is capable of expression of the xylose isomerase in the host cell.

Methods for expressing a heterologous xylose isomerase sequence in a cell are well known to those skilled in the art.

Accordingly, a cell of the invention is a recombinant cell. That is to say, a cell of the invention comprises, or is transformed with or is genetically modified with a nucleotide sequence that does not naturally occur in the cell in question.

Techniques for the recombinant expression of xylose isomerase in a cell, as well as for the additional genetic modifications of a cell of the invention are well known to those skilled in the art. Typically such techniques involve transformation of a cell with nucleic acid construct comprising the relevant sequence. Such methods are, for example, known from standard handbooks, such as Sambrook and Russel (2001) "Molecular Cloning: A Laboratory Manual (3rd edition), Cold Spring Harbor Laboratory, Cold Spring Harbor Laboratory Press, or F. Ausubel et al., eds., "Current protocols in molecular biology", Green Publishing and Wiley Interscience, New York (1987). Methods for transformation and genetic modification of fungal host cells are known from e.g. EP-A-0635 574, WO 98/46772, WO 99/60102, WO 00/37671, WO90/14423, EP-A-0481008, EP-A-0635574 and U.S. Pat. No. 6,265,186.

Most episomal or 2μ plasmids are relatively unstable, being lost in approximately $10^{-2}$ or more cells after each generation. Even under conditions of selective growth, only 60% to 95% of the cells retain the episomal plasmid. The copy number of most episomal plasmids ranges from 10-40 per cell of cir$^+$ hosts. However, the plasmids are not equally distributed among the cells, and there is a high variance in the copy number per cell in populations. Strains transformed with integrative plasmids are extremely stable, even in the absence of selective pressure. However, plasmid loss can occur at approximately $10^{-3}$ to $10^{-4}$ frequencies by homologous recombination between tandemly repeated DNA, leading to looping out of the vector sequence. Preferably, the vector design in the case of stable integration is thus, that upon loss of the selection marker genes (which also occurs by intramolecular, homologous recombination) that looping out of the integrated construct is no longer possible. Preferably the genes are thus stably integrated. Stable integration is herein defined as integration into the genome, wherein looping out of the integrated construct is no longer possible. Preferably selection markers are absent.

Typically, the nucleic acid construct may be a plasmid, for instance a low copy plasmid or a high copy plasmid. The cell according to the present invention may comprise a single or multiple copies of the nucleotide sequence encoding a xylose isomerase, for instance by multiple copies of a nucleotide construct or by use of construct which has multiple copies of the xylose isomerase sequence.

The nucleic acid construct may be maintained episomally and thus comprise a sequence for autonomous replication, such as an autosomal replication sequence sequence. A suitable episomal nucleic acid construct may e.g. be based on the yeast 2μ or pKD1 plasmids (Gleer et al., 1991, Biotechnology 9: 968-975), or the AMA plasmids (Fierro et al., 1995, Curr Genet. 29:482-489). Alternatively, each nucleic acid construct may be integrated in one or more copies into the genome of the cell. Integration into the cell's genome may occur at random by non-homologous recombination but preferably, the nucleic acid construct may be integrated into the cell's genome by homologous recombination as is well known in the art (see e.g. WO90/14423, EP-A-0481008, EP-A-0635 574 and U.S. Pat. No. 6,265, 186).

Typically, the xylose isomerase encoding sequence will be operably linked to one or more nucleic acid sequences, capable of providing for or aiding the transcription and/or translation of the xylose isomerase sequence.

The term "operably linked" refers to a juxtaposition wherein the components described are in a relationship permitting them to function in their intended manner. For instance, a promoter or enhancer is operably linked to a coding sequence the said promoter or enhancer affects the transcription of the coding sequence.

As used herein, the term "promoter" refers to a nucleic acid fragment that functions to control the transcription of one or more genes, located upstream with respect to the direction of transcription of the transcription initiation site of the gene, and is structurally identified by the presence of a binding site for DNA-dependent RNA polymerase, transcription initiation sites and any other DNA sequences known to one of skilled in the art. A "constitutive" promoter is a promoter that is active under most environmental and developmental conditions. An "inducible" promoter is a promoter that is active under environmental or developmental regulation.

The promoter that could be used to achieve the expression of a nucleotide sequence coding for an enzyme according to the present invention, may be not native to the nucleotide sequence coding for the enzyme to be expressed, i.e. a promoter that is heterologous to the nucleotide sequence (coding sequence) to which it is operably linked. The promoter may, however, be homologous, i.e. endogenous, to the host cell.

Suitable promoters in this context include both constitutive and inducible natural promoters as well as engineered promoters, which are well known to the person skilled in the art. Suitable promoters in eukaryotic host cells may be GAL7, GAL10, or GAL1, CYC1, HIS3, ADH1, PGL, PH05, GAPDH, ADC1, TRP1, URA3, LEU2, ENO1, TPI1, and AOX1. Other suitable promoters include PDC1, GPD1, PGK1, TEF1, and TDH3.

In a cell of the invention, the 3'-end of the nucleotide acid sequence encoding xylose isomerase preferably is operably linked to a transcription terminator sequence. Preferably the terminator sequence is operable in a host cell of choice, such as e.g. the yeast species of choice. In any case the choice of the terminator is not critical; it may e.g. be from any yeast gene, although terminators may sometimes work if from a non-yeast, eukaryotic, gene. Usually a nucleotide sequence encoding the xylose isomerase comprises a terminator. Preferably, such terminators are combined with mutations that prevent nonsense mediated mRNA decay in the host cell of the invention (see for example: Shirley et al., 2002, Genetics 161:1465-1482).

The transcription termination sequence further preferably comprises a polyadenylation signal.

Optionally, a selectable marker may be present in a nucleic acid construct suitable for use in the invention. As used herein, the term "marker" refers to a gene encoding a trait or a phenotype which permits the selection of, or the screening for, a host cell containing the marker. The marker gene may be an antibiotic resistance gene whereby the appropriate antibiotic can be used to select for transformed cells from among cells that are not transformed. Examples of suitable antibiotic resistance markers include e.g. dihydrofolate reductase, hygromycin-B-phosphotransferase, 3'-O-phosphotransferase II (kanamycin, neomycin and G418 resistance). Although the of antibiotic resistance markers may be most convenient for the transformation of polyploid host cells, preferably however, non-antibiotic resistance markers are used, such as auxotrophic markers (URA3, TRPI, LEU2) or the S. pombe TPI gene (described by Russell P R, 1985, Gene 40: 125-130). In a preferred embodiment the host cells transformed with the nucleic acid constructs are marker gene free. Methods for constructing recombinant marker gene free microbial host cells are disclosed in EP-A-O 635 574 and are based on the use of bidirectional markers such as the A. nidulans amdS (acetamidase) gene or the yeast URA3 and LYS2 genes. Alternatively, a screenable marker such as Green Fluorescent Protein, lacL, luciferase, chloramphenicol acetyltransferase, beta-glucuronidase may be incorporated into the nucleic acid constructs of the invention allowing to screen for transformed cells.

Optional further elements that may be present in the nucleic acid constructs suitable for use in the invention include, but are not limited to, one or more leader sequences, enhancers, integration factors, and/or reporter genes, intron sequences, centromers, telomers and/or matrix attachment (MAR) sequences. The nucleic acid constructs of the invention may further comprise a sequence for autonomous replication, such as an ARS sequence.

Preferably, the xylose isomerase is expressed in the cytosol. Cytosolic expression may be achieved by deletion or modification of a mitochondrial or peroxisomal targeting signal.

A cell of the invention may be any suitable cell, such as a prokaryotic cell, such as a bacterium, or a eukaryotic cell. Typically, the cell will be a eukaryotic cell, for example a yeast or a filamentous fungus.

Yeasts are herein defined as eukaryotic microorganisms and include all species of the subdivision Eumycotina (Alexopoulos, C. J., 1962, In: Introductory Mycology, John Wiley & Sons, Inc., New York) that predominantly grow in unicellular form.

Yeasts may either grow by budding of a unicellular thallus or may grow by fission of the organism. A preferred yeast as a cell of the invention may belong to the genera *Saccharomyces, Kluyveromyces, Candida, Pichia, Schizosaccharomyces, Hansenula, Kloeckera, Schwanniomyces* or *Yarrowia*. Preferably the yeast is one capable of anaerobic fermentation, more preferably one capable of anaerobic alcoholic fermentation.

Filamentous fungi are herein defined as eukaryotic microorganisms that include all filamentous forms of the subdivision Eumycotina. These fungi are characterized by a vegetative mycelium composed of chitin, cellulose, and other complex polysaccharides.

The filamentous fungi of the suitable for use as a cell of the present invention are morphologically, physiologically, and genetically distinct from yeasts. Filamentous fungal cells may be advantageously used since most fungi do not require sterile conditions for propagation and are insensitive to bacteriophage infections. Vegetative growth by filamentous fungi is by hyphal elongation and carbon catabolism of most filamentous fungi is obligately aerobic. Preferred filamentous fungi as a host cell of the invention may belong to the genus *Aspergillus, Trichoderma, Humicola, Acremoniurra, Fusarium* or *Penicillium*. More preferably, the filamentous fungal cell may be a *Aspergillus niger, Aspergillus oryzae*, a *Penicillium chrysogenum*, or *Rhizopus oryzae* cell.

Over the years suggestions have been made for the introduction of various organisms for the production of bio-ethanol from crop sugars. In practice, however, all major bio-ethanol production processes have continued to use the yeasts of the genus *Saccharomyces* as ethanol producer. This is due to the many attractive features of *Saccharomyces* species for industrial processes, i.e., a high acid-, ethanol- and osmo-tolerance, capability of anaerobic growth, and of course its high alcoholic fermentative capacity. Preferred yeast species as host cells include *S. cerevisiae, S. bulderi, S. barnetti, S. exiguus, S. uvarum, S. diastaticus, K. lactis, K. marxianus* or *K. fragilis*.

A cell of the invention may be able to convert plant biomass, celluloses, hemicelluloses, pectins, rhamnose, galactose, fucose, maltose, maltodextrines, ribose, ribulose, or starch, starch derivatives, sucrose, lactose and glycerol, for example into fermentable sugars. Accordingly, a cell of the invention may express one or more enzymes such as a cellulase (an endocellulase or an exocellulase), a hemicellulase (an endo- or exo-xylanase or arabinase) necessary for the conversion of cellulose into glucose monomers and hemicellulose into xylose and arabinose monomers, a pectinase able to convert pectins into glucuronic acid and galacturonic acid or an amylase to convert starch into glucose monomers.

A cell of the invention is preferably is a host capable of active or passive xylose transport into the cell.

Preferably, a cell of the invention:
is capable of active glycolysis; and/or
shows flux through the pentose phosphate pathway; and/or
displays xylulose kinase activity so that the xylulose isomerised from xylose may be metabolised to pyruvate.

The cell further preferably comprises those enzymatic activities required for conversion of pyruvate to a desired fermentation product, such as ethanol, butanol, lactic acid, 3-hydroxy-propionic acid, acrylic acid, acetic acid, succinic acid, citric acid, fumaric acid, malic acid, itaconic acid, an amino acid, 1,3-propane-diol, ethylene, glycerol, a β-lactam antibiotic or a cephalosporin.

A preferred cell of the invention is a cell that is naturally capable of alcoholic fermentation, preferably, anaerobic alcoholic fermentation. A cell of the invention preferably has a high tolerance to ethanol, a high tolerance to low pH (i.e. capable of growth at a pH lower than about 5, about 4, about 3, or about 2.5) and towards organic acids like lactic acid, acetic acid or formic acid and/or sugar degradation products such as furfural and hydroxy-methylfurfural and/or a high tolerance to elevated temperatures.

Any of the above characteristics or activities of a cell of the invention may be naturally present in the cell or may be introduced or modified by genetic modification.

The nucleotide sequence encoding a xylose isomerase is typically expressed or is capable of being expressed in active form in the transformed host cell. Thus, expression of the nucleotide sequence in the host cell produces an active xylose isomerase, typically with a specific activity of at least about 10 U xylose isomerase activity per mg protein at about 30° C., preferably at least about 20, at least about 25, at least about 30, at least about 50, at least about 100, at least about 200, at least about 300, at least about 500, at least about 750 or at least about 1000 U per mg at about 30° C. The specific activity of the xylose isomerase expressed in the transformed host cell is herein defined as the amount of xylose isomerase activity units per mg protein of cell free lysate of the host cell, e.g. a yeast cell free lysate. Determination of the xylose isomerase activity, amount of protein and preparation of the cell free lysate are as described herein. Preferably, expression of the nucleotide sequence encoding the xylose isomerase in the host cell produces a xylose isomerase with a $K_m$ for xylose that is less than 50, 40, 30 or 25 mM, more preferably, the $K_m$ for xylose is about 20 mM or less.

A cell of the invention may comprise one or more genetic modifications that increases the flux of the pentose phosphate pathway. In particular, the genetic modification(s) may lead to an increased flux through the non-oxidative part pentose phosphate pathway. A genetic modification that causes an increased flux of the non-oxidative part of the pentose phosphate pathway is herein understood to mean a modification that increases the flux by at least a factor of about 1.1, about 1.2, about 1.5, about 2, about 5, about 10 or about 20 as compared to the flux in a strain which is genetically identical except for the genetic modification causing the increased flux. The flux of the non-oxidative part of the pentose phosphate pathway may be measured by growing the modified host on xylose as sole carbon source, determining the specific xylose consumption rate and subtracting the specific xylitol production rate from the specific xylose consumption rate, if any xylitol is produced. However, the flux of the non-oxidative part of the pentose phosphate pathway is proportional with the growth rate on xylose as sole carbon source, preferably with the anaerobic growth rate on xylose as sole carbon source. There is a linear relation between the growth rate on xylose as sole carbon source ($\mu_{max}$) and the flux of the non-oxidative part of the pentose phosphate pathway. The specific xylose consumption rate ($Q_s$) is equal to the growth rate ($\mu$) divided by the yield of biomass on sugar ($Y_{xs}$) because the yield of biomass on sugar is constant (under a given set of conditions: anaerobic, growth medium, pH, genetic background of the strain, etc.; i.e. $Q_s = \mu/Y_{xs}$). Therefore the increased flux of the non-oxidative part of the pentose phosphate pathway may be deduced from the increase in maximum growth rate under these conditions unless transport (uptake is limiting).

One or more genetic modifications that increase the flux of the pentose phosphate pathway may be introduced in the host cell in various ways. These including e.g. achieving higher steady state activity levels of xylulose kinase and/or one or more of the enzymes of the non-oxidative part pentose phosphate pathway and/or a reduced steady state level of unspecific aldose reductase activity. These changes in steady state activity levels may be effected by selection of mutants (spontaneous or induced by chemicals or radiation) and/or by recombinant DNA technology e.g. by overexpression or inactivation, respectively, of genes encoding the enzymes or factors regulating these genes.

In a preferred host cell, the genetic modification comprises overexpression of at least one enzyme of the (non-oxidative part) pentose phosphate pathway. Preferably the enzyme is selected from the group consisting of the enzymes encoding for ribulose-5-phosphate isomerase, ribulose-5-phosphate epimerase, transketolase and transaldolase. Various combinations of enzymes of the (non-oxidative part) pentose phosphate pathway may be overexpressed. E.g. the enzymes that are overexpressed may be at least the enzymes ribulose-5-phosphate isomerase and ribulose-5-phosphate epimerase; or at least the enzymes ribulose-5-phosphate isomerase and transketolase; or at least the enzymes ribulose-5-phosphate isomerase and transaldolase; or at least the enzymes ribulose-5-phosphate epimerase and transketolase; or at least the enzymes ribulose-5-phosphate epimerase and transaldolase; or at least the enzymes transketolase and transaldolase; or at least the enzymes ribulose-5-phosphate epimerase, transketolase and transaldolase; or at least the enzymes ribulose-5-phosphate isomerase, transketolase and transaldolase; or at least the enzymes ribulose-5-phosphate isomerase, ribulose-5-phosphate epimerase, and transaldolase; or at least the enzymes ribulose-5-phosphate isomerase, ribulose-5-phosphate epimerase, and transketolase. In one embodiment of the invention each of the enzymes ribulose-5-phosphate isomerase, ribulose-5-phosphate epimerase, transketolase and transaldolase are overexpressed in the host cell. More preferred is a host cell in which the genetic modification comprises at least overexpression of both the enzymes transketolase and transaldolase as such a host cell is already capable of anaerobic growth on xylose. In fact, under some conditions host cells overexpressing only the transketolase and the transaldolase already have the same anaerobic growth rate on xylose as do host cells that overexpress all four of the enzymes, i.e. the ribulose-5-phosphate isomerase, ribulose-5-phosphate epimerase, transketolase and transaldolase. Moreover, host cells overexpressing both of the enzymes ribulose-5-phosphate isomerase and ribulose-5-phosphate epimerase are preferred over host cells overexpressing only the isomerase or only the epimerase as overexpression of only one of these enzymes may produce metabolic imbalances.

The enzyme "ribulose 5-phosphate epimerase" (EC 5.1.3.1) is herein defined as an enzyme that catalyses the epimerisation of D-xylulose 5-phosphate into D-ribulose 5-phosphate and vice versa. The enzyme is also known as phosphoribulose epimerase; erythrose-4-phosphate isomerase; phosphoketopentose 3-epimerase; xylulose phosphate 3-epimerase; phosphoketopentose epimerase; ribulose 5-phosphate 3-epimerase; D-ribulose phosphate-3-epimerase; D-ribulose 5-phosphate epimerase; D-ribulose-5-P 3-epimerase; D-xylulose-5-phosphate 3-epimerase; pentose-5-phosphate 3-epimerase; or D-ribulose-5-phosphate 3-epimerase. A ribulose 5-phosphate epimerase may be further defined by its amino acid sequence. Likewise a ribulose 5-phosphate epimerase may be defined by a nucleotide sequence encoding the enzyme as well as by a nucleotide sequence hybridising to a reference nucleotide sequence encoding a ribulose 5-phosphate epimerase. The nucleotide sequence encoding for ribulose 5-phosphate epimerase is herein designated RPE1.

The enzyme "ribulose 5-phosphate isomerase" (EC 5.3.1.6) is herein defined as an enzyme that catalyses direct isomerisation of D-ribose 5-phosphate into D-ribulose 5-phosphate and vice versa. The enzyme is also known as phosphopentosisomerase; phosphoriboisomerase; ribose phosphate isomerase; 5-phosphoribose isomerase; D-ribose 5-phosphate isomerase; D-ribose-5-phosphate ketol-isomerase; or D-ribose-5-phosphate aldose-ketose-isomerase. A ribulose 5-phosphate isomerase may be further defined by its amino acid sequence. Likewise a ribulose 5-phosphate isomerase may be defined by a nucleotide sequence encoding the enzyme as well as by a nucleotide sequence hybridising to a reference nucleotide sequence encoding a ribulose 5-phosphate isomerase. The nucleotide sequence encoding for ribulose 5-phosphate isomerase is herein designated RPI1.

The enzyme "transketolase" (EC 2.2.1.1) is herein defined as an enzyme that catalyses the reaction: D-ribose 5-phosphate+D-xylulose 5-phosphate<–>sedoheptulose 7-phosphate+D-glyceraldehyde 3-phosphate and vice versa. The enzyme is also known as glycolaldehydetransferase or sedoheptulose-7-phosphate:D-glyceraldehyde-3-phosphate glycolaldehydetransferase. A transketolase may be further defined by its amino acid. Likewise a transketolase may be defined by a nucleotide sequence encoding the enzyme as well as by a nucleotide sequence hybridising to a reference nucleotide sequence encoding a transketolase. The nucleotide sequence encoding for transketolase is herein designated TKL1.

The enzyme "transaldolase" (EC 2.2.1.2) is herein defined as an enzyme that catalyses the reaction: sedoheptulose 7-phosphate+D-glyceraldehyde 3-phosphate<–>D-erythrose 4-phosphate+D-fructose 6-phosphate and vice versa. The enzyme is also known as dihydroxyacetonetransferase; dihydroxyacetone synthase; formaldehyde transketolase; or sedoheptulose-7-phosphate:D-glyceraldehyde-3-phosphate glyceronetransferase. A transaldolase may be further defined by its amino acid sequence. Likewise a transaldolase may be defined by a nucleotide sequence encoding the enzyme as well as by a nucleotide sequence hybridising to a reference nucleotide sequence encoding a transaldolase. The nucleotide sequence encoding for transaldolase from is herein designated TAL1.

Various means are known to those skilled in the art for expression and overexpression of enzymes in a cell of the invention. In particular, an enzyme may be overexpressed by increasing the copy number of the gene coding for the enzyme in the host cell, e.g. by integrating additional copies of the gene in the host cell's genome, by expressing the gene from an episomal multicopy expression vector or by introducing a episomal expression vector that comprises multiple copies of the gene.

Alternatively, overexpression of enzymes in the host cells of the invention may be achieved by using a promoter that is not native to the sequence coding for the enzyme to be overexpressed, i.e. a promoter that is heterologous to the coding sequence to which it is operably linked. Although the promoter preferably is heterologous to the coding sequence to which it is operably linked, it is also preferred that the promoter is homologous, i.e. endogenous to the host cell. Preferably the heterologous promoter is capable of producing a higher steady state level of the transcript comprising the coding sequence (or is capable of producing more transcript molecules, i.e. mRNA molecules, per unit of time) than is the promoter that is native to the coding sequence, preferably under conditions where xylose or xylose and glucose are available as carbon sources, more preferably as major carbon sources (i.e. more than 50% of the available carbon source consists of xylose or xylose and glucose), most preferably as sole carbon sources. Suitable promoters in this context include both constitutive and inducible natural promoters as well as engineered promoters. A preferred promoter for use in the present invention will in addition be insensitive to catabolite (glucose) repression and/or will preferably not require xylose for induction. Promotors having these characteristics are widely available and known to the skilled person. Suitable examples of such promoters include e.g. promoters from glycolytic genes, such as the phosphofructokinase (PFK), triose phosphate isomerase (TPI), glyceraldehyde-3-phosphate dehydrogenase (GPD, TDH3 or GAPDH), pyruvate kinase (PYK), phosphoglycerate kinase (PGK) promoters from yeasts or filamentous fungi; more details about such promoters from yeast may be found in (WO 93/03159). Other useful promoters are ribosomal protein encoding gene promoters, the lactase gene promoter (LAC4), alcohol dehydrogenase promoters (ADHI, ADH4, and the like), and the enolase promoter (ENO). Other promoters, both constitutive and inducible, and enhancers or upstream activating sequences will be known to those of skill in the art. The promoters used in the host cells of the invention may be modified, if desired, to affect their control characteristics.

The coding sequence used for overexpression of the enzymes mentioned above may preferably be homologous to the host cell of the invention. However, coding sequences that are heterologous to the host cell of the invention may be used.

Overexpression of an enzyme, when referring to the production of the enzyme in a genetically modified host cell, means that the enzyme is produced at a higher level of specific enzymatic activity as compared to the unmodified host cell under identical conditions. Usually this means that the enzymatically active protein (or proteins in case of multi-subunit enzymes) is produced in greater amounts, or rather at a higher steady state level as compared to the unmodified host cell under identical conditions. Similarly this usually means that the mRNA coding for the enzymatically active protein is produced in greater amounts, or again rather at a higher steady state level as compared to the unmodified host cell under identical conditions. Overexpression of an enzyme is thus preferably determined by measuring the level of the enzyme's specific activity in the host cell using appropriate enzyme assays as described herein. Alternatively, overexpression of the enzyme may be determined indirectly by quantifying the specific steady state level of enzyme protein, e.g. using antibodies specific for the enzyme, or by quantifying the specific steady level of the mRNA coding for the enzyme. The latter may particularly be suitable for enzymes of the pentose phosphate pathway for which enzymatic assays are not easily feasible as substrates for the enzymes are not commercially available. Preferably in a host cell of the invention, an enzyme to be overexpressed is overexpressed by at least a factor of about 1.1, about 1.2, about 1.5, about 2, about 5, about 10 or about 20 as compared to a strain which is genetically identical except for the genetic modification causing the overexpression. It is to be understood that these levels of overexpression may apply to the steady state level of the enzyme's activity, the steady state level of the enzyme's protein as well as to the steady state level of the transcript coding for the enzyme.

A cell of the invention may comprise one or more genetic modifications that increase the specific xylulose kinase activity. Preferably the genetic modification or modifications causes overexpression of a xylulose kinase, e.g. by overexpression of a nucleotide sequence encoding a xylulose kinase. The gene encoding the xylulose kinase may be endogenous to the host cell or may be a xylulose kinase that is heterologous to the host cell. A nucleotide sequence used for overexpression of xylulose kinase in the host cell of the invention is a nucleotide sequence encoding a polypeptide with xylulose kinase activity.

The enzyme "xylulose kinase" (EC 2.7.1.17) is herein defined as an enzyme that catalyses the reaction ATP+D-xylulose=ADP+D-xylulose 5-phosphate. The enzyme is also known as a phosphorylating xylulokinase, D-xylulokinase or ATP:D-xylulose 5-phosphotransferase. A xylulose kinase of the invention may be further defined by its amino acid sequence. Likewise a xylulose kinase may be defined by a nucleotide sequence encoding the enzyme as well as by a nucleotide sequence hybridising to a reference nucleotide sequence encoding a xylulose kinase.

In a cell of the invention, a genetic modification or modifications that increase(s) the specific xylulose kinase activity may be combined with any of the modifications increasing the flux of the pentose phosphate pathway as described above. This is not, however, essential.

Thus, a host cell of the invention may comprise only a genetic modification or modifications that increase the specific xylulose kinase activity. The various means available in the art for achieving and analysing overexpression of a xylulose kinase in the host cells of the invention are the same as described above for enzymes of the pentose phosphate pathway. Preferably in the host cells of the invention, a xylulose kinase to be overexpressed is overexpressed by at least a factor of about 1.1, about 1.2, about 1.5, about 2, about 5, about 10 or about 20 as compared to a strain which is genetically identical except for the genetic modification(s) causing the overexpression. It is to be understood that these levels of overexpression may apply to the steady state level of the enzyme's activity, the steady state level of the enzyme's protein as well as to the steady state level of the transcript coding for the enzyme.

A cell of the invention may comprise one or more genetic modifications that reduce unspecific aldose reductase activity in the host cell. Preferably, unspecific aldose reductase activity is reduced in the host cell by one or more genetic modifications that reduce the expression of or inactivates a gene encoding an unspecific aldose reductase. Preferably, the genetic modification(s) reduce or inactivate the expression of each endogenous copy of a gene encoding an unspecific aldose reductase in the host cell. Host cells may comprise multiple copies of genes encoding unspecific aldose reductases as a result of di-, poly- or aneu-ploidy, and/or the host cell may contain several different (iso) enzymes with aldose reductase activity that differ in amino acid sequence and that are each encoded by a different gene. Also in such instances preferably the expression of each gene that encodes an unspecific aldose reductase is reduced or inactivated. Preferably, the gene is inactivated by deletion of at least part of the gene or by disruption of the gene, whereby in this context the term gene also includes any non-coding sequence up- or down-stream of the coding sequence, the (partial) deletion or inactivation of which results in a reduction of expression of unspecific aldose reductase activity in the host cell.

A nucleotide sequence encoding an aldose reductase whose activity is to be reduced in the host cell of the invention is a nucleotide sequence encoding a polypeptide with aldose reductase activity.

In the host cells of the invention, genetic modification that reduces unspecific aldose reductase activity in the host cell may be combined with any of the modifications increasing the flux of the pentose phosphate pathway and/or with any of the modifications increasing the specific xylulose kinase activity in the host cells as described above. This is not, however, essential.

Thus, a host cell of the invention comprising only a genetic modification or modifications that reduce(s) unspecific aldose reductase activity in the host cell is specifically included in the invention.

The enzyme "aldose reductase" (EC 1.1.1.21) is herein defined as any enzyme that is capable of reducing xylose or xylulose to xylitol. In the context of the present invention an aldose reductase may be any unspecific aldose reductase that is native (endogenous) to a host cell of the invention and that is capable of reducing xylose or xylulose to xylitol. Unspecific aldose reductases catalyse the reaction:

The enzyme has a wide specificity and is also known as aldose reductase; polyol dehydrogenase (NADP$^+$); alditol:

NADP oxidoreductase; alditol:NADP⁺ 1-oxidoreductase; NADPH-aldopentose reductase; or NADPH-aldose reductase.

A particular example of such an unspecific aldose reductase that is endogenous to *S. cerevisiae* and that is encoded by the GRE3 gene (Traff et al., 2001, Appl. Environ. Microbiol. 67: 5668-74). Thus, an aldose reductase of the invention may be further defined by its amino acid sequence. Likewise an aldose reductase may be defined by the nucleotide sequences encoding the enzyme as well as by a nucleotide sequence hybridising to a reference nucleotide sequence encoding an aldose reductase.

A cell of the invention may be adapted to xylose utilisation by selection of mutants, either spontaneous or induced (e.g. by radiation or chemicals), for growth on xylose, preferably on xylose as sole carbon source, and more preferably under anaerobic conditions. Selection of mutants may be performed by techniques including serial passaging of cultures as e.g. described by Kuyper et al. (2004, FEMS Yeast Res. 4: 655-664) or by cultivation under selective pressure in a chemostat culture. In a preferred host cell of the invention at least one of the genetic modifications described above, including modifications obtained by selection of mutants, confer to the host cell the ability to grow on xylose as carbon source, preferably as sole carbon source, and preferably under anaerobic conditions. Preferably the modified host cell produce essentially no xylitol, e.g. the xylitol produced is below the detection limit or e.g. less than about 5, about 2, about 1, about 0.5, or about 0.3% of the carbon consumed on a molar basis.

A cell of the invention may have the ability to grow on xylose as sole carbon source at a rate of at least about 0.05, about 0.1, about 0.2, about 0.25 or about 0.3 $h^{-1}$ under aerobic conditions, or, if applicable, at a rate of at least about 0.03, about 0.05, about 0.07, about 0.08, about 0.09, about 0.1, about 0.12, about 0.15 or about 0.2 $h^{-1}$ under anaerobic conditions. Preferably the modified host cell has the ability to grow on a mixture of glucose and xylose (in a 1:1 weight ratio) as sole carbon source at a rate of at least about 0.05, about 0.1, about 0.2, about 0.25 or about 0.3 $h^{-1}$ under aerobic conditions, or, if applicable, at a rate of at least about 0.03, about 0.05, about 0.1, about 0.12, about 0.15, or about 0.2 $h^{-1}$ under anaerobic conditions.

A cell of the invention may have a specific xylose consumption rate of at least about 200, about 250, about 300, about 346, about 350, about 400, about 500, about 600, about 750, or about 1000 mg xylose/g cells/h. A cell of the invention may have a yield of fermentation product (such as ethanol) on xylose that is at least about 40, about 50, about 55, about 60, about 70, about 80, about 85, about 90, about 95 about 98 or about 99% of the host cell's yield of fermentation product (such as ethanol) on glucose. More preferably, the yield of a fermentation product (such as ethanol) of a cell of the invention on xylose may be equal to the cell's yield of fermentation product (such as ethanol) on glucose. Likewise, the cell's biomass yield on xylose may be at least about 40, about 50, about 55, about 60, about 70, about 80, about 85, about 90, about 95, about 98 or about 99% of the host cell's biomass yield on glucose. More preferably, the cell's biomass yield on xylose, may be equal to the host cell's biomass yield on glucose. It is understood that in the comparison of yields on glucose and xylose both yields are compared under aerobic conditions or both under anaerobic conditions.

A cell of the invention may be capable of using arabinose. A cell of the invention may, therefore, be capable of converting L-arabinose into L-ribulose and/or xylulose 5-phosphate and/or into a desired fermentation product, for example one of those mentioned herein.

Organisms, for example *S. cerevisiae* strains, able to produce ethanol from L-arabinose may be produced by modifying a cell introducing the araA (L-arabinose isomerase), araB (L-ribulokinase) and araD (L-ribulose-5-P4-epimerase) genes from a suitable source. Such genes may be introduced into a cell of the invention is order that it is capable of using arabinose. Such an approach is described in WO2003/095627.

A cell of the invention may be a cell suitable for the production of ethanol. A cell of the invention may, however, be suitable for the production of fermentation products other than ethanol. Such non-ethanolic fermentation products include in principle any bulk or fine chemical that is producible by a eukaryotic microorganism such as a yeast or a filamentous fungus.

Such fermentation products may be, for example, butanol, lactic acid, 3-hydroxy-propionic acid, acrylic acid, acetic acid, succinic acid, citric acid, malic acid, fumaric acid, itaconic acid, an amino acid, 1,3-propane-diol, ethylene, glycerol, a β-lactam antibiotic or a cephalosporin. A preferred modified host cell of the invention for production of non-ethanolic fermentation products is a host cell that contains a genetic modification that results in decreased alcohol dehydrogenase activity.

In a further aspect the invention relates to fermentation processes in which the modified host cells of the invention are used for the fermentation of a carbon source comprising a source of xylose, such as xylose. In addition to a source of xylose the carbon source in the fermentation medium may also comprise a source of glucose. The source of xylose or glucose may be xylose or glucose as such or may be any carbohydrate oligo- or polymer comprising xylose or glucose units, such as e.g. lignocellulose, xylans, cellulose, starch and the like. For release of xylose or glucose units from such carbohydrates, appropriate carbohydrases (such as xylanases, glucanases, amylases and the like) may be added to the fermentation medium or may be produced by the modified host cell. In the latter case the modified host cell may be genetically engineered to produce and excrete such carbohydrases. An additional advantage of using oligo- or polymeric sources of glucose is that it enables to maintain a low(er) concentration of free glucose during the fermentation, e.g. by using rate-limiting amounts of the carbohydrases. This, in turn, will prevent repression of systems required for metabolism and transport of non-glucose sugars such as xylose.

In a preferred process the modified host cell ferments both the xylose and glucose, preferably simultaneously in which case preferably a modified host cell is used which is insensitive to glucose repression to prevent diauxic growth. In addition to a source of xylose (and glucose) as carbon source, the fermentation medium will further comprise the appropriate ingredient required for growth of the modified host cell. Compositions of fermentation media for growth of microorganisms such as yeasts are well known in the art. The fermentation process is a process for the production of a fermentation product such as e.g. ethanol, butanol, lactic acid, 3-hydroxy-propionic acid, acrylic acid, acetic acid, succinic acid, citric acid, malic acid, fumaric acid, itaconic acid, an amino acid, 1,3-propane-diol, ethylene, glycerol, a β-lactam antibiotic, such as Penicillin G or Penicillin V and fermentative derivatives thereof, and a cephalosporin.

The fermentation process may be an aerobic or an anaerobic fermentation process. An anaerobic fermentation process is herein defined as a fermentation process run in the absence of oxygen or in which substantially no oxygen is consumed, preferably less than about 5, about 2.5 or about 1 mmol/L/h, more preferably 0 mmol/L/h is consumed (i.e. oxygen consumption is not detectable), and wherein organic molecules serve as both electron donor and electron acceptors. In the absence of oxygen, NADH produced in glycolysis and biomass formation, cannot be oxidised by oxidative phosphorylation. To solve this problem many microorganisms use pyruvate or one of its derivatives as an electron and hydrogen acceptor thereby regenerating $NAD^+$.

Thus, in a preferred anaerobic fermentation process pyruvate is used as an electron (and hydrogen acceptor) and is reduced to fermentation products such as ethanol, butanol, lactic acid, 3-hydroxy-propionic acid, acrylic acid, acetic acid, succinic acid, citric acid, malic acid, fumaric acid, an amino acid, 1,3-propane-diol, ethylene, glycerol, a βlactam antibiotic and a cephalosporin.

The fermentation process is preferably run at a temperature that is optimal for the modified host cell. Thus, for most yeasts or fungal host cells, the fermentation process is performed at a temperature which is less than about 42° C., preferably less than about 38° C. For yeast or filamentous fungal host cells, the fermentation process is preferably performed at a temperature which is lower than about 35, about 33, about 30 or about 28° C. and at a temperature which is higher than about 20, about 22, or about 25° C.

A preferred process is a process for the production of a ethanol, whereby the process comprises the steps of: (a) fermenting a medium containing a source of xylose with a modified host cell as defined above, whereby the host cell ferments xylose to ethanol; and optionally, (b) recovery of the ethanol. The fermentation medium may also comprise a source of glucose that is also fermented to ethanol. In the process the volumetric ethanol productivity is preferably at least about 0.5, about 1.0, about 1.5, about 2.0, about 2.5, about 3.0, about 5.0 or about 10.0 g ethanol per liter per hour. The ethanol yield on xylose and/or glucose in the process preferably is at least about 50, about 60, about 70, about 80, about 90, about 95 or about 98%. The ethanol yield is herein defined as a percentage of the theoretical maximum yield.

The invention also relates to a process for producing a fermentation product, such as a product selected from the group consisting of butanol lactic acid, 3-hydroxy-propionic acid, acrylic acid, acetic acid, succinic acid, citric acid, malic acid, fumaric acid, itaconic acid, an amino acid, 1,3-propane-diol, ethylene, glycerol, a β-lactam antibiotic and a cephalosporin. The process preferably comprises fermenting a medium containing a source of xylose with a modified host cell as defined herein above, whereby the host cell ferments xylose to the fermentation product.

The invention also provides a process for producing a fermentation product, such as a product selected from the group consisting of ethanol, butanol, lactic acid, 3-hydroxy-propionic acid, acrylic acid, acetic acid, succinic acid, citric acid, malic acid, fumaric acid, itaconic acid, an amino acid, 1,3-propane-diol, ethylene, glycerol, a β-lactam antibiotic and a cephalosporin. The process preferably comprises fermenting a medium containing at least a source of xylose and a source of L-arabinose with a cell as defined above which is able to use both of xylose and L-arabinose such that the cell ferments xylose and L-arabinose to the fermentation product.

The invention also provides a process for producing a fermentation product, such as a product selected from the group consisting of ethanol, butanol, lactic acid, 3-hydroxy-propionic acid, acrylic acid, acetic acid, succinic acid, citric acid, malic acid, fumaric acid, itaconic acid, an amino acid, 1,3-propane-diol, ethylene, glycerol, a β-lactam antibiotic and a cephalosporin. The process preferably comprises fermenting a medium containing at least a source of xylose and a source of L-arabinose with a cell as defined above and a cell able to use L-arabinose, whereby each cell ferments xylose and/or arabinose to the fermentation product.

A process of the invention may also comprise recovery of the fermentation product. The medium with which the process is carried out may also contain a source of glucose.

The process according to the present invention may be run under aerobic and anaerobic conditions. Preferably, the process is carried out under micro-aerophilic or oxygen limited conditions.

An anaerobic fermentation process is herein defined as a fermentation process run in the absence of oxygen or in which substantially no oxygen is consumed, preferably less than about 5, about 2.5 or about 1 mmol/L/h, and wherein organic molecules serve as both electron donor and electron acceptors.

An oxygen-limited fermentation process is a process in which the oxygen consumption is limited by the oxygen transfer from the gas to the liquid. The degree of oxygen limitation is determined by the amount and composition of the ingoing gasflow as well as the actual mixing/mass transfer properties of the fermentation equipment used. Preferably, in a process under oxygen-limited conditions, the rate of oxygen consumption is at least about 5.5, more preferably at least about 6, such as at least 7 mmol/L/h.

The following Examples illustrate the invention:

EXAMPLES

General Molecular Biology Techniques

Unless indicated otherwise, the methods used are standard biochemical techniques. Examples of suitable general methodology textbooks include Sambrook et al., Molecular Cloning, a Laboratory Manual (1989) and Ausubel et al., Current Protocols in Molecular Biology (1995), John Wiley & Sons, Inc.

Growth experiments were performed using either Verduyn medium (Verduyn, 1992) or YEPh-medium (10 g/l yeast extract, 20 g/l phytone), supplemented with sugars as indicated in the examples. For solid YEPh medium, 20 g/l agar was added to the liquid medium prior to sterilization.

Transformation of Yeast Cells with Circular DNA

Yeast transformation was done according to the method described by Chen et al (Current Genetics (1992), Volume 21, Number 1, 83-84) in case of plasmid DNA.

Transformation of Yeast Cells with Linear DNA Fragments by Electroporation

Yeast cells were cultured by inoculating 25 ml of YEPh-medium containing 2% glucose with a single yeast colony. The flask was incubated overnight at 30° C., 280 rpm.

The optical density at 600 nm was determined and the amount needed to obtain an optical density of 0.2 was transferred to 100 ml YEPh-medium with 2% glucose. The cells were grown for 4 to 5 hours at 30° C., 280 rpm, in order to reach an optical density of approximately 1.2 to 1.3, which corresponds to 2 to 3 generations. Cells were collected by centrifugation and resuspended in 28 ml TE (10 mM Tris.HCl, 1 mM EDTA, pH 7.5). 3 ml of a 1M LiAC solution (set at pH 7.5 with diluted HAc) was added. The cells were gently shaken in a rotary incubator (150 rpm, 30° C.) for 45 minutes. After addition of 500 µl of a 1M DTT (dithiothreitol) solution, the cells were incubated once more under these conditions, for 15 minutes. The volume was made up to 100 ml with sterile, ice-cold milliQ water. The cells were collected by centrifugation.

The supernatant was discarded and the pelleted cells were washed with 50 ml of sterile, ice cold milliQ water, and collected by centrifugation. A subsequent washing treatment was done with 30 ml of an ice cold 1M sorbitol solution. After centrifugation, the supernatant was discarded and the cell pellet was resuspended in 4 ml of an ice cold 1M sorbitol solution. After centrifugation, the supernatant was discarded and the cell pellet was resuspended in 300 µl of an ice cold 1M sorbitol solution.

For each transformation, 40 µl of the cell suspension was transferred into ice cold Eppendorf tubes. The transforming DNA and 5 µg salmon sperm DNA (as carrier DNA) was added, together in a maximum volume of 20 µl. The DNA should be dissolved in TE. The Eppendorf tube was carefully tapped in order to mix the content gently. Subsequently, the content was transferred to a pre-chilled (on ice) electroporation cuvette with a gap of 0.2 cm and a pulse (using e.g. a BioRad Electroporation Device) at 1.5 kV, 200 Ohm and 25 µF was applied. The pulse time should be around 5 ms.

The cells were immediately transferred to 200 µl 1M sorbitol. Subsequently, 4 ml of YEPh 2% glucose was added and the cell suspension was incubated at 30° C. for 1 hour. After this hour, the cells were collected by centrifugation, the supernatant was discarded and the pellet resuspended in 4 ml of 1M sorbitol. The cells were again collected by centrifugation, the supernatant was discarded and the pellet resuspended in 300 µl of 1M sorbitol. The cells were diluted as appropriate and used in selective media.

Ethanol Production

Pre-cultures were prepared by inoculating 25 ml Verduyn-medium (Verduyn et al., Yeast 8:501-517, 1992) supplemented with 2% glucose in a 100 ml shake flask with a frozen stock culture or a single colony from an agar plate. After incubation at 30° C. in an orbital shaker (280 rpm) for approximately 24 hours, this culture was harvested and used for determination of carbon dioxide evolution and ethanol production experiments.

Cultivations for ethanol production were performed at 30° C. in 100 ml synthetic model medium (Verduyn-medium (Verduyn et al., Yeast 8:501-517, 1992) with 5% glucose, 5% xylose, 3.5% arabinose, 1% galactose and 0.5% mannose) in the BAM (Biological Activity Monitor, Halotec, the Netherlands). The pH of the medium was adjusted to 4.2 with 2 M NaOH/$H_2SO_4$ prior to sterilisation. The synthetic medium for anaerobic cultivation was supplemented with 0.01 g/l ergosterol and 0.42 g/l Tween 80 dissolved in ethanol (Andreasen and Stier. J. Cell Physiol. 41:23-36, 1953; and Andreasen and Stier. J. Cell Physiol. 43:271-281, 1954). The medium was inoculated at an initial $OD^{600}$ of approximately 2. Cultures were stirred by a magnetic stirrer. Anaerobic conditions developed rapidly during fermentation as the cultures were not aerated. Carbon dioxide production was monitored constantly. Sugar conversion and product formation (ethanol, glycerol) was analyzed by NMR. Growth was monitored by following optical density of the culture at 600 nm on a LKB Ultrospec K spectrophotometer.

Example 1

Construction of Xylose Isomerase Expression Vector

A synthetic codon-pair optimized xylA gene was designed based on the primary amino acid sequence and synthesized by GeneArt (Regensburg, Germany). Codon-pair optimization was performed as described previously (WO2008000632). The nucleotide sequence is included in here as SEQ ID NO 1, the corresponding amino acid sequence as SEQ ID NO 2.

Figure 1:
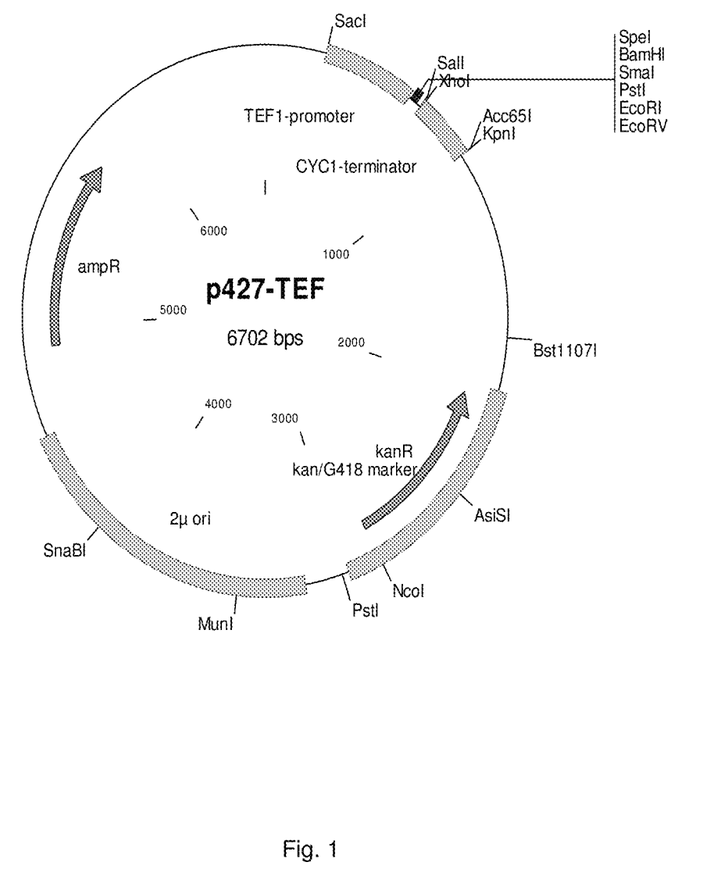
FIG. 1 sets out the plasmid map of p427-TEF encoding xylose isomerase from *Clostridium beijerinckii* for expression in *Saccharomyces cerevisiae*. CpO denotes codon pair optimized.

The open reading frame was cloned into the yeast shuttle vector p427-TEF (FIG. 1; DualSystems Biotech, Schlieren, Switzerland) using the restriction enzymes SpeI and XmaI.

The plasmid was called pPWT215.

Example 2

Transformation of BIE104P1 with pPWT215

A *S. cerevisiae* strain, BIE104P1 (MATa URA3 HIS3 LEU2 TRP1 MAL2-8 SUC2 GRE3::[TPI1p-TAL1_ADH1p-TKL1_PGI1p-RPE1_ENO1p-RKI1]) as disclosed in WO2009109633, in which the GRE3-gene was replaced by the genes of the non-oxidative part of the pentose phosphate pathway was transformed with the plasmid pPWT215, using the One-Step Yeast Transformation method described by Chen et al (1992). As a negative control, milliQ was used. The final pellet of the transformation procedure was resuspended in 1 ml of YEPh 2% glucose (see above). 50 µl of this transformation mixture was plated on a YEPh agar plate supplemented with 2% glucose and 200 µg G418/ml. The remaining 950 µl was transferred to a 100 ml shake flask containing 25 ml Verduyn medium, supplemented with 2% xylose, 10 µg G418/ml and 250 µl of a Pen-Strep solution (Gibco/Invitrogen). The inoculated flasks (mock transformation and plasmid transformation) were incubated in a rotary shaker at 30° C. and 280 rpm. The optical density was followed in time.

Example 3

Growth Experiment

Figure 2:
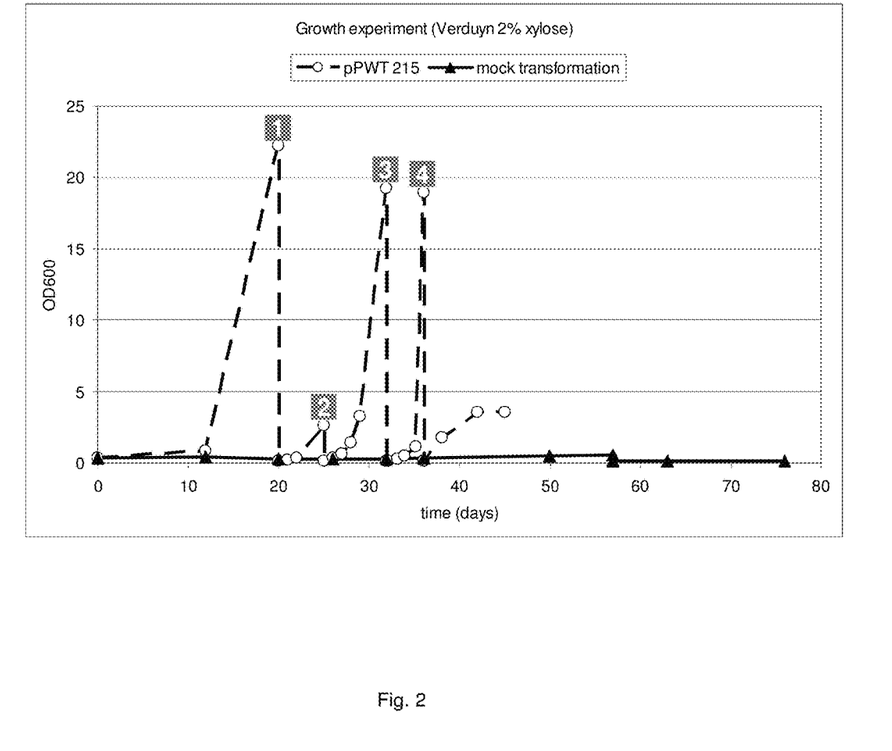
FIG. 2 sets out a growth curve of BIE104P1 transformed with pPWT215 on 2% xylose as sole carbon source, and of the reference strain transformed with no DNA in the plasmid (mock transformation). The numbers "1" and "2" indicate the transfer of an aliquot of the culture to fresh medium. All cultures were incubated in the presence of air, except the last one (after the second transfer).

The progression of the growth experiment following transformation is shown in FIG. 2.

During the first ten days of the growth experiment, the optical density at 600 nm of the cultures hardly increased. After 20 days (indicated with "1" in FIG. 2) the optical density of the plasmid transformed cell culture reached a value larger than 20. Subsequently, an amount of the culture was transferred to a fresh aliquot of 25 ml Verduyn medium containing 2% xylose, 10 µg G418/ml and 250 µl Pen-Strep. As is clear from FIG. 2, 4 transfers were made. The growth experiment was performed in the presence of air, except for the last culture, after the fourth transfer, which was performed in a shake flask with a waterlock (anaerobic conditions).

From FIG. 2 it can be concluded that yeast cells of strain BIE104P1 transformed with pPWT215 have gained the ability to utilize xylose as a sole carbon and energy source, while yeast cells of the same strain, mock transformed, did not show an increase in optical density, hence cannot grow on xylose.

Example 4

Construction of a Pentose Fermenting Cell

*S. cerevisae* strain BIE292 is a derivative of strain BIE201. The construction of this strain has been disclosed in PCT/EP2011/056242, example 7. It is the result of a back-cross of strain BIE201, a strain which is optimized by transformation and adaptive evolution for efficient arabinose fermentation, and its parent, prior to adaptive evolution, strain BIE104A2P1a. Strain BIE292 expresses the genes araA, araB and araD from *Lactobacillus plantarum* and the non-oxidative pentose phosphate pathway genes TAL1, TKL1, RPE1 and RKI1 constitutively and the GRE3 gene encoding aldose reductase has been deleted. In addition, BIE292 has an amplification of this arabinose cassette on chromosome VII and the SNP in the GAL80 gene (nucleotide change A436C, where the A of the startcodon ATG is 1).

Subsequently, strain BIE292 was transformed with PCR fragments of the codon-pair optimized xylA gene, including promoter and terminator sequences, flanked with 100 bp overlapping regions to Ty1 sequences in the genome. The xylA expression cassette was amplified by PCR using pPWT215 as a template. The PCR reaction was performed with the primer sequences SEQ ID NO 3 and SEQ ID NO 4 using Phusion DNA polymerase (Finnzymes) using the instructions of the supplier. The amplified expression cassette was ethanol precipitated and stored at −20° C. prior to use.

The precipitated DNA was collected by centrifugation and the DNA pellet was washed with 70% ethanol and subsequently air dried. The DNA was dissolved at a concentration of approximately 1 μg of DNA/μl in TE-buffer.

Yeast strain BIE292 was grown in YEPh-medium containing 2% glucose. Competent cells were prepared for electroporation, as described above. Electrocompetent cells were transformed with 20 μg PCR product. As a negative control, milliQ water was used.

Transformation mixes of both the xylA- and mock transformation were directly transferred to 4 different shake flasks each containing 25 ml Verduyn medium supplemented with 2% xylose and 250 μl pen/strep. As no dominant selection marker is used, selection of correct transformants on plate after transformation was not performed.

The eight shake flasks were incubated in a rotary shaker at 30° C. and 280 rpm. Growth was monitored by measuring the optical density at 600 nm frequently.

Example 5

Selection and Characterization of a Pentose Fermenting Yeast Strain

If the culture described in Example 4 has reached an optical density at 600 nm greater than 15, an aliquot of 250 μl is transferred to a flask containing Verduyn medium supplemented with 2% xylose. The optical density at 600 nm is monitored frequently. The growth rate is determined with the use of the optical density data.

After several cycles of inoculation on xylose containing media, Verduyn medium containing 2% arabinose as a carbon source is being used, in order to keep the selective pressure on arabinose utilization. Likewise, a flask containing Verduyn medium supplemented with a mixture of hexoses (i.e. glucose, galactose and/or mannose) and pentoses (i.e. arabinose and/or xylose) is used. The culturing experiments are initially performed under aerobic conditions, but are subsequently performed under anaerobic conditions, for instance when the growth rate exceeds a value of about 0.07 per hour or higher, on both arabinose and xylose.

After several cycles of growth and re-inoculation under anaerobic conditions, an aliquot of the cultures is diluted to about 100-1000 colony forming units (CFU) per milliliter and subsequently aliquots of 10-100 μl are plated out on YEPh-agar plates containing 2% glucose. Plates are incubated for at least 48 hours at 30° C., or until single colonies are visible.

Single colony isolates are tested in the BAM (vide supra). Single colony isolates are selected on basis of the ability to ferment all five sugars efficiently, as is inferred from the carbon dioxide profile and the NMR data of the sugars, ethanol and by-products.

The best strains are characterized by genetic and molecular biology techniques known to those skilled in the art, such as PCR, Southern blot(s), FIGE and resequencing.

Example 6

Selection and Characterization of a Pentose Fermenting Yeast Strain

When the culture described in Example 4 had reached an optical density at 600 nm greater than 10, an aliquot of 25 μl was transferred to a shake flask containing Verduyn medium supplemented with 2% xylose. The optical density was monitored frequently and the growth rate was determined with the use of these data. When the culture reached an optical density at 600 nm greater than 15, and aliquot of the culture was transferred to a shake flask containing Verduyn medium supplemented with 2% xylose and the shake flask was closed with a water lock enabling anaerobic culturing. From this point, incubations were performed in an orbital shaker at 30° C. and 100 rpm. Growth of the culture was monitored by measuring the optical density at 600 nm and the growth rate was calculated based on these data. When the optical density at 600 nm of the culture reached a value greater than 3.75, an aliquot of the culture was transferred to a shake flask containing Verduyn medium supplemented with 2% arabinose. The shake flask was closed with a water lock. In case the culture reached an optical density at 600 nm with a value greater than 5, an aliquot of the culture was again transferred to a shake flask containing Verduyn medium supplemented with 2% xylose and this shake flask was closed with a water lock. A typical result of this growth experiment is given in FIG. 3.

Figure 3:
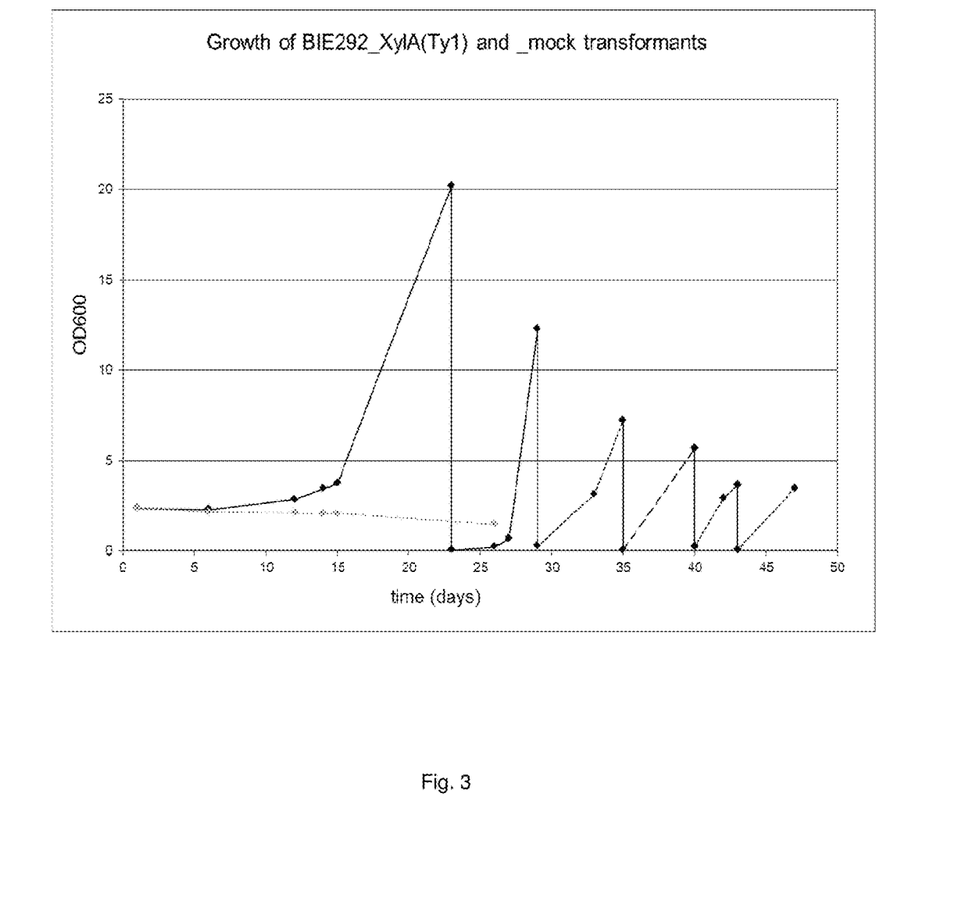
FIG. 3 sets out growth curves of Strain BIE292XI (*C. beyerinckii*) (black line) and a mock strain (grey line), from example 6.

As is clear from FIG. 3, transformation of BIE292 with XyIA from *Clostridium beyerinckii* enabled this strain to rapidly obtain a xylose-consuming phenotype, while the mock transformation did not result in xylose-consuming cells.

Table 1 presents the growth rates of *S. cerevisiae* strains transformed with xylose isomerase genes from several organisms. Strain BIE292XI (*C. beyerinckii*) demonstrated the highest growth rate under aerobic conditions upon initial growth on xylose as sole carbon source after transformation. In addition, BIE292XI (*C. beyerinckii*) was the only strain able to grow on xylose under anaerobic conditions without extensive evolutionary engineering.

TABLE 1

Growth rates of BIE292XI(*C. beyerinckii*) and publically available data of a *Saccharomyces cerevisiae* strains transformed with XI of *Clostridium phytofermentans* (ref. 1), *Orpinomyces* (ref. 2), *Piromyces* (RWB202) (ref. 3), and *Thermus thermophilus* (ref. 4), upon initial growth on xylose.

| Xylose isomerase | Aerobic | Anaerobic |
|---|---|---|
| C. beyerincki | 0.061 $h^{-1}$ | 0.056 $h^{-1}$ |
| C. phytofermentans | 0.039 $h^{-1}$ | — |
| Orpinomyces | 0.01 $h^{-1}$ | — |
| Piromyces | 0.005 $h^{-1}$ | — |
| T. thermophilus | — | — |

The data presented in the table above are all obtained from different strain backgrounds.

— indicates not measured or not tested.

For the *S. cerevisiae* strain harboring XI from *T. Thermophilus* it is noted that comsumption of xylose was observed, but comsumption levels were too low to support growth.

The invention claimed is:

1. A *Saccharomyces cerevisiae* cell comprising a heterologous nucleotide sequence encoding a polypeptide comprising at least 95% sequence identity to the amino acid sequence of SEQ ID NO: 2 and having xylose isomerase activity, wherein said *Saccharomyces cerevisiae* cell can grow on xylose as sole carbon source under aerobic and anaerobic conditions.

2. The *Saccharomyces cerevisiae* cell of claim 1, wherein said heterologous nucleotide sequence encoding said polypeptide having xylose isomerase activity is obtained from a cell of the genus *Clostridium*.

3. The *Saccharomyces cerevisiae* cell of claim 1, wherein said *Saccharomyces cerevisiae* cell further comprises at least one genetic modification resulting in:
   a. an increase in transport of xylose in the cell;
   b. an increase in xylulose kinase activity;
   c. an increase in flux through the pentose phosphate pathway;
   d. a decrease in aldose reductase activity;
   e. a decrease in sensitivity to catabolite repression;
   f. an increase in tolerance to ethanol, osmolarity or organic acids; or
   g. a reduced production of by-products, as compared with a *Saccharomyces cerevisiae* cell without said at least one genetic modification, wherein said at least one genetic modification is selected from the group consisting of overexpression of at least one gene encoding an enzyme of the non-oxidative part of the pentose phosphate pathway, overexpression of a gene encoding a xylulose kinase, expression of genes araA, araB and araD from *Lactobacillus plantarum*, inactivation of a gene encoding an endogenous unspecific aldose reductase, and a combination thereof.

4. The *Saccharomyces cerevisiae* cell to of claim 3, wherein said at least one genetic modification is overexpression of at least one gene encoding an enzyme of the non-oxidative part of the pentose phosphate pathway.

5. The *Saccharomyces cerevisiae* cell to of claim 4, wherein said gene is a gene encoding a ribulose-5-phosphate isomerase, a ribulose-5-phosphate epimerase, a transketolase, and/or a transaldolase.

6. The *Saccharomyces cerevisiae* cell of claim 3, wherein said at least one genetic modification is overexpression of a gene encoding a xylulose kinase.

7. The *Saccharomyces cerevisiae* cell of claim 3, wherein said at least one genetic modification is inactivation of a gene encoding an endogenous unspecific aldose reductase.

8. The *Saccharomyces cerevisiae* cell of claim 1, wherein said *Saccharomyces cerevisiae* cell further comprises overexpression of TAL1, TKL1, RPE1 and RKI1 genes and the ability to use L-arabinose.

9. The *Saccharomyces cerevisiae* cell of claim 3, comprising at least one constitutively expressed or constitutively overexpressed gene stably integrated into the genome of said *Saccharomyces cerevisiae* cell.

10. A process for producing a fermentation product comprising:
    fermenting a medium containing xylose in the presence of the *Saccharomyces cerevisiae* cell of claim 1 under conditions whereby said fermentation product is produced.

11. The process of claim 10, wherein said fermentation product is ethanol, butanol, lactic acid, 2-hydroxy-propionic acid, acrylic acid, acetic acid, succinic acid, citric acid, malic acid, fumaric acid, itaconic acid, an amino acid, 1,3-propane-diol, ethylene, glycerol, a β-lactam antibiotic and/or a cephalosporin.

12. The process of claim 10, wherein said process is anaerobic.

13. The *Saccharomyces cerevisiae* cell of claim 1, wherein said heterologous nucleotide sequence encodes a polypeptide comprising at least 97% sequence identity to the amino acid sequence of SEQ ID NO: 2 and having xylose isomerase activity.

\* \* \* \* \*

SEQUENCE LISTING

<160> NUMBER OF SEQ ID NOS: 4

<210> SEQ ID NO 1
<211> LENGTH: 1374
<212> TYPE: DNA
<213> ORGANISM: Artificial Sequence
<220> FEATURE:
<223> OTHER INFORMATION: codon pair optimised xylose isomerase sequence
      from Clostridium beijerinckii

<400> SEQUENCE: 1

```
actagtaaaa acacatacat aaactaaaaa tgagagaata cttcgaaaac gtttccaaga      60
tcaactacga aggtgctaac tccaagaacc catactcttt caagtactac aacccagatg     120
aaatcattgg tgacaaggct atgaaggaac acttgagatt tgctctatcc tactggcaca     180
ctttaaccgc caccggtgct gatcctttcg gtgttggtac tatgatcaga ccatgggact     240
ctgaaaccaa tgaaatggac ttggccaagg ccagaatgga agctgctttc gaattgatgg     300
acaaattgaa catcgaatac ttctgtttcc acgaccgtga cattgcccca gaaggtaaga     360
ctttgcaaga aaccaacaag aacttggatg aaattgttgc tctatgtaag tctttgatga     420
agaagtacaa caagaaattg ttgtggggta ctgctaactg tttcaccaac ccacgttacg     480
ttcacggtgc tggtacttcc tgtaacgctg atgttttcgc ttatgctgct gctcaaatca     540
agaaggccat cgaaatcacc aaggaattgg atggtgaaaa ctacgtcttt tggggtggta     600
gagaaggtta cgaaacttta ttgaacactg acatgggttt ggaattggac aactttgcta     660
gattattgca aatggctgtc gactacgcca aggaaattgg tttcaccggt caattcttga     720
ttgaaccaaa gccaaaggaa ccaaccaagc accaatacga tttcgatgct gctaccgttt     780
tgggtttctt gaagaactac aacttggaca atacttcaa ggttaacatt gaagctaacc      840
atgccacttt agctcaacac actttccaac acgaattgca cttcgccaga atcaacaaat     900
tcttgggttc tattgacgct aaccaaggtg acccattatt gggttgggac actgaccaat     960
tcccaaccaa catctacgat gctactttgg ctatgtacga aatcttgaaa aatggtggtt    1020
tggctccagg tggtgtcaac ttcgactcca aggtcagaag agcttctttc gaaaaggaag    1080
atttgttctt ggcttacatt gctggtatgg acacctttgc caagggtttg agagttgctt    1140
acaagttgtt ggaaaacggt gacttggaag atttcatcaa ggaaaaatac tcttctttca    1200
ccgaaggtat tggtaaggaa atcgtcgaag gtaaggtcgg tttcaaggaa ttggaagcct    1260
acgctttgaa caacacccca atcatcaaca gtctggtag acaagaatta ttggaatcca    1320
ttgtcaacca atacatcttc gaagatcaca ataagccgc ggtcgcgacc cggg           1374
```

<210> SEQ ID NO 2
<211> LENGTH: 441
<212> TYPE: PRT
<213> ORGANISM: Clostridium beijerinckii

<400> SEQUENCE: 2

```
Met Arg Glu Tyr Phe Glu Asn Val Ser Lys Ile Asn Tyr Glu Gly Ala
1               5                   10                  15

Asn Ser Lys Asn Pro Tyr Ser Phe Lys Tyr Tyr Asn Pro Asp Glu Ile
            20                  25                  30

Ile Gly Asp Lys Ala Met Lys Glu His Leu Arg Phe Ala Leu Ser Tyr
        35                  40                  45

Trp His Thr Leu Thr Ala Thr Gly Ala Asp Pro Phe Gly Val Gly Thr
    50                  55                  60
```

```
Met Ile Arg Pro Trp Asp Ser Glu Thr Asn Glu Met Asp Leu Ala Lys
 65                  70                  75                  80

Ala Arg Met Glu Ala Ala Phe Glu Leu Met Asp Lys Leu Asn Ile Glu
                 85                  90                  95

Tyr Phe Cys Phe His Asp Arg Asp Ile Ala Pro Glu Gly Lys Thr Leu
            100                 105                 110

Gln Glu Thr Asn Lys Asn Leu Asp Glu Ile Val Ala Leu Cys Lys Ser
        115                 120                 125

Leu Met Lys Lys Tyr Asn Lys Lys Leu Leu Trp Gly Thr Ala Asn Cys
    130                 135                 140

Phe Thr Asn Pro Arg Tyr Val His Gly Ala Gly Thr Ser Cys Asn Ala
145                 150                 155                 160

Asp Val Phe Ala Tyr Ala Ala Ala Gln Ile Lys Lys Ala Ile Glu Ile
                165                 170                 175

Thr Lys Glu Leu Asp Gly Glu Asn Tyr Val Phe Trp Gly Gly Arg Glu
            180                 185                 190

Gly Tyr Glu Thr Leu Leu Asn Thr Asp Met Gly Leu Glu Leu Asp Asn
        195                 200                 205

Phe Ala Arg Leu Leu Gln Met Ala Val Asp Tyr Ala Lys Glu Ile Gly
    210                 215                 220

Phe Thr Gly Gln Phe Leu Ile Glu Pro Lys Pro Lys Glu Pro Thr Lys
225                 230                 235                 240

His Gln Tyr Asp Phe Asp Ala Ala Thr Val Leu Gly Phe Leu Lys Asn
                245                 250                 255

Tyr Asn Leu Asp Lys Tyr Phe Lys Val Asn Ile Glu Ala Asn His Ala
            260                 265                 270

Thr Leu Ala Gln His Thr Phe Gln His Glu Leu His Phe Ala Arg Ile
        275                 280                 285

Asn Lys Phe Leu Gly Ser Ile Asp Ala Asn Gln Gly Asp Pro Leu Leu
    290                 295                 300

Gly Trp Asp Thr Asp Gln Phe Pro Thr Asn Ile Tyr Asp Ala Thr Leu
305                 310                 315                 320

Ala Met Tyr Glu Ile Leu Lys Asn Gly Gly Leu Ala Pro Gly Gly Val
                325                 330                 335

Asn Phe Asp Ser Lys Val Arg Arg Ala Ser Phe Glu Lys Glu Asp Leu
            340                 345                 350

Phe Leu Ala Tyr Ile Ala Gly Met Asp Thr Phe Ala Lys Gly Leu Arg
        355                 360                 365

Val Ala Tyr Lys Leu Leu Glu Asn Gly Asp Leu Glu Asp Phe Ile Lys
    370                 375                 380

Glu Lys Tyr Ser Ser Phe Thr Glu Gly Ile Gly Lys Glu Ile Val Glu
385                 390                 395                 400

Gly Lys Val Gly Phe Lys Glu Leu Glu Ala Tyr Ala Leu Asn Asn Asn
                405                 410                 415

Pro Ile Ile Asn Lys Ser Gly Arg Gln Glu Leu Leu Gly Ser Ile Val
            420                 425                 430

Asn Gln Tyr Ile Phe Glu Asp His Lys
        435                 440

<210> SEQ ID NO 3
<211> LENGTH: 123
<212> TYPE: DNA
<213> ORGANISM: Artificial Sequence
<220> FEATURE:
<223> OTHER INFORMATION: forward primer
```

```
<400> SEQUENCE: 3
tttctcatgg tagcgcctgt gcttcggtta cttctaagga agtccacaca aatcaagatc    60
cgttagacgt ttcagcttcc aaaacagaag aatgtgagac caaaagctgg agctcatagc   120
ttc                                                                 123

<210> SEQ ID NO 4
<211> LENGTH: 121
<212> TYPE: DNA
<213> ORGANISM: Artificial Sequence
<220> FEATURE:
<223> OTHER INFORMATION: reverse primer

<400> SEQUENCE: 4
tggaggtggt actgaagcag gttgaggaga ggcatgatgg gggttctctg gaacagctga    60
tgaagcaggt gttgttgtct gttgagagtt agccttagtg gtaccggccg caaattaaag   120
c                                                                   121
```